United States Patent
La Fuente et al.

(10) Patent No.: US 9,289,300 B2
(45) Date of Patent: Mar. 22, 2016

(54) LA FUENTE POROUS IMPLANT MATRIX

(71) Applicants: Henry La Fuente, Oklahoma City, OK (US); Brandon Ray La Fuente, Oklahoma City, OK (US); Jonathan Patrick Dickinson, Carrollton, TX (US)

(72) Inventors: Henry La Fuente, Oklahoma City, OK (US); Brandon Ray La Fuente, Oklahoma City, OK (US); Jonathan Patrick Dickinson, Carrollton, TX (US)

(73) Assignee: La Fuente's Ocular Prosthetics, LLC, Oklahoma City, OK (US)

(*) Notice: Subject to any disclaimer, the term of this patent is extended or adjusted under 35 U.S.C. 154(b) by 118 days.

(21) Appl. No.: 14/078,304

(22) Filed: Nov. 12, 2013

(65) Prior Publication Data
US 2014/0277514 A1    Sep. 18, 2014

Related U.S. Application Data

(60) Provisional application No. 61/724,925, filed on Nov. 10, 2012.

(51) Int. Cl.
| | | |
|---|---|---|
| A61F 2/14 | (2006.01) |
| A61F 2/28 | (2006.01) |
| A61L 27/06 | (2006.01) |
| A61L 27/04 | (2006.01) |
| A61L 27/08 | (2006.01) |
| A61L 27/16 | (2006.01) |
| A61L 27/18 | (2006.01) |
| A61L 27/50 | (2006.01) |
| A61L 27/56 | (2006.01) |
| A61F 2/30 | (2006.01) |

(52) U.S. Cl.
CPC .............. *A61F 2/28* (2013.01); *A61F 2/2814* (2013.01); *A61L 27/042* (2013.01); *A61L 27/06* (2013.01); *A61L 27/08* (2013.01); *A61L 27/16* (2013.01); *A61L 27/18* (2013.01); *A61L 27/50* (2013.01); *A61L 27/56* (2013.01); *A61F 2/141* (2013.01); *A61F 2/2803* (2013.01); *A61F 2/2875* (2013.01); *A61F 2002/2878* (2013.01); *A61F 2002/2889* (2013.01); *A61F 2002/3092* (2013.01); *A61L 2430/02* (2013.01); *A61L 2430/16* (2013.01); *A61L 2430/30* (2013.01)

(58) Field of Classification Search
None
See application file for complete search history.

(56) References Cited

U.S. PATENT DOCUMENTS

| | | | |
|---|---|---|---|
| 4,280,233 | A | 7/1981 | Raab |
| 6,346,121 | B1 | 2/2002 | Hicks et al. |
| 2007/0016163 | A1 | 1/2007 | Santini, Jr. et al. |
| 2013/0237747 | A1 | 9/2013 | Linares et al. |
| 2013/0282140 | A1 | 10/2013 | Ringeisen et al. |

*Primary Examiner* — David H Willse
*Assistant Examiner* — Javier Blanco
(74) *Attorney, Agent, or Firm* — Hall Estill Attorneys at Law

(57) ABSTRACT

A porous surgical implant constructed of a nonbiodegradable polymer that is molded to form an omnidirectional vascularization frame. The frame defines a porous external surface and a plurality of internal longitudinally extending capillaries of a substantially constant porosity throughout the implant. The internal capillaries are in fluid communication with the external porous surface and thereby configured to absorb a fluid adjacent the implant.

4 Claims, 11 Drawing Sheets

LA FUENTE PORUS IMPLANT MATRIX

RELATED APPLICATION

This application claims the benefit of the earlier filing date of U.S. provisional patent application Ser. No. 61/724,925 filed on Nov. 10, 2012.

BACKGROUND

This technology generally relates to the construction of alloplastic surgical implants, and is more particularly directed to an improved material and associated process for constructing a surgical implant. Implantable devices are widely used to replace or augment body tissue in surgical procedures, such as in surgical repair or cosmetic surgery. Finding the ideally constructed implant has eluded all the previously attempted solutions in this field of technology.

Generally, nonporous implants are problematic because the body tends to form a fibrovascular capsule around the solid surface, effectively walling off the nonporous implant from the body. The walling off precludes fibrovascular tissue ingrowth, so the nonporous implant does not biologically integrate with the surrounding body tissue. The fibrovascular capsule can contract, disadvantageously causing a nonporous implant to change shape and/or orientation. Due to the lack of biological integration, nonporous implants can migrate to an undesirable position and/or orientation, and can also cause resorption of the underlying bone. All these factors diminish the desired functionality of the implant. Furthermore, space inside the fibrovascular capsule that becomes infected cannot be reached by the body's immunities, often requiring surgical removal of the nonporous implant.

Porous implants have been developed that are aimed at addressing these concerns. Although improvements have been made in previously attempted solutions, the ideal porous implant would be an alloplast that is economically manufacturable, yet biologically superior in promoting fibrovascular tissue ingrowth while being infection resistant, nonantigenic, and noninflammatory. It is to these advantages that the embodiments of the present invention are directed.

SUMMARY

Some embodiments of the present technology contemplate a porous surgical implant constructed of a nonbiodegradable polymer that is molded to form an omnidirectional vascularization frame. The frame defines a porous external surface and a plurality of internal longitudinally extending capillaries of a substantially constant porosity throughout the implant. The internal capillaries are in fluid communication with the external porous surface and thereby configured to absorb a fluid adjacent the implant.

Some embodiments of the present technology contemplate a porous surgical implant molded into an actuate shape resembling a human body tissue. The implant is constructed of an acrylic polymer defining an omnidirectional vascularization frame having a substantially constant porosity. The acrylic polymer is formed from a liquid polymer that is homogenously mixed with grains of table salt and then cured into a solid polymer and table salt mixture. The frame surfaces are defined entirely by removal of the grains of table salt from the solid polymer after curing.

Some embodiments of the present technology contemplate a method including steps of:

preparing a liquid polymer; adding a selected amount of cubic-shaped porogens to the liquid polymer so that a ratio of porogen volume to polymer volume is greater than 1;
mixing the porogens and the liquid polymer together forming a homogenously blended mixture;
molding the blended mixture to produce a solid mixture that is molded into an arcuate shape resembling a human body tissue; and leaching the porogens out of the solid mixture to form a surgically implantable tissue frame.

DETAILED DESCRIPTION

Initially, it is to be appreciated that this disclosure is by way of example only, not by limitation. The surgical implant concepts herein are not limited to use or application with any specific type or method of surgical procedure. Thus, although the instrumentalities described herein are for the convenience of explanation, shown and described with respect to exemplary embodiments, it will be appreciated that the principles herein may be applied equally in other types of surgical implants and corresponding procedures, such that an enumeration of all possible instrumentalities is unnecessary for the skilled artisan to understand the scope of the claimed invention.

Figure 1:
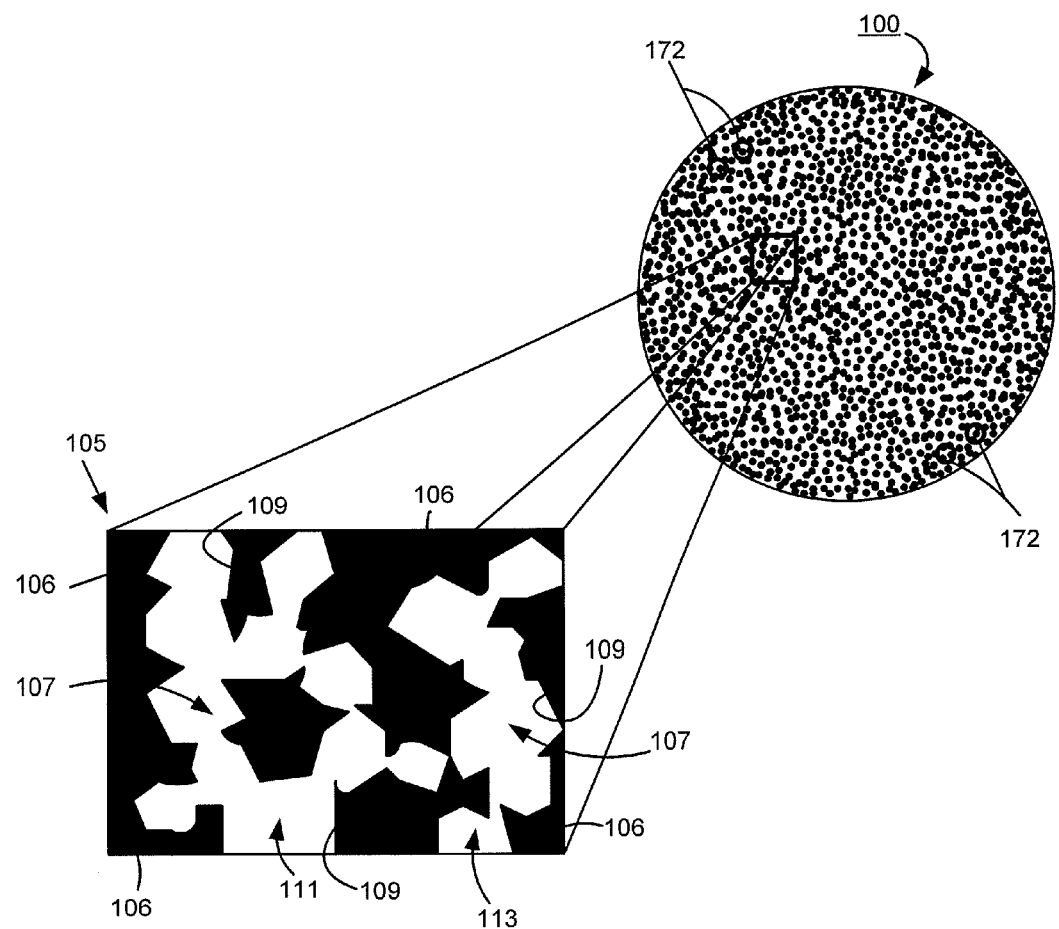
FIG. 1 depicts a spherical porous implant in accordance with embodiments of the present invention, including an expanded detail.

FIG. 1 depicts a substantially spherical porous implant 100 that is constructed in accordance with illustrative embodiments of the present invention. The implant 100 is molded to have an arcuate porous surface forming a size and shape resembling a human eye. That is, for the purpose of these illustrative embodiments the implant 100 has an exterior arcuate surface that is substantially spherical, and sized to make the implant 100 useable as an ophthalmic implant in an evisceration or enucleation surgical procedure. Preferably, the surgeon would be able to select a particular implant 100 from a set of differently sized implants, such as can range from about 14 millimeters (mm) diameter to about 22 mm diameter, to match the particular volume augmentation needed.

By saying the implant 100 is "molded," means a viscous polymer is injected (or otherwise placed) into a die set which, by the application of heat and/or pressure, cures the viscous polymer into a non-biodegradable solid polymer that gets its external shape from the configuration of the die set. In alternative embodiments, some of which discussed below, the die set is configured so that the molded arcuate outer surface can resemble some other body tissue, such as a bone or muscle tissue. "Molded" does not preclude performing secondary operations on the implant before or after curing, such as cutting, folding, splicing, and the like. Generally, the porous polymer of this technology is moldable into any of a number of different shapes corresponding to different types of surgical implants. In whatever shape, the porous polymer implant is constructed of a material that superiorly supports fibrovascular tissue ingrowth to become biologically integrated with the surrounding tissue in which it is implanted.

With respect to the particular example of FIG. 1, the implant 100 must effectively reproduce the volume, position, and motility of a natural eye; and it must not extrude or migrate. To achieve that the surgeon attaches the extraocular muscles to the implant 100 to function as they do when attached to the natural eye. The muscles are attached by shallow suturing to the implant 100. The porous implant 100 promotes fibrovascular tissue ingrowth sufficient to biologically integrate the implant 100 with the muscles.

Importantly, to achieve the improved vascularity performance of this technology, the molded porous polymer forms an internal frame structure 105—all the solid polymer inside and forming the exterior surface of the implant 100. The frame 105 is an interconnected network of polymeric struts 106 throughout the entirety of the implant 100. The struts 106 preferably form segments of planar surfaces 109 of the polymeric material for reasons explained below. The hollow spaces 107 between struts 106 define an omnidirectional matrix of interconnected interstitial capillaries 111, 113 within the frame 105. The sizes and arrangements of the hollow spaces 107 are substantially constant by homogenously mixing the porogens throughout the implant 100, as described below. That makes the porosity substantially constant throughout the implant 100. For purposes of this description and meaning of the claims the term "porosity" means the volume of the matrix divided by the total volume of the implant 100:

$$\text{porosity} = \frac{V_V}{V_T}$$

where $V_V$ is the volume of the void (or matrix) and $V_T$ is the combined volume of the void and the frame 105.

Figure 2:
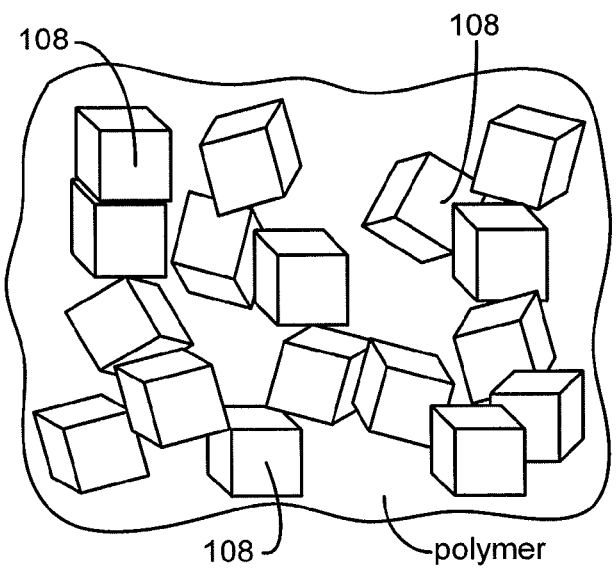
FIG. 2 is an enlarged view of a portion of a homogenous mixture of straight-sided porogens in a liquid polymer.

FIG. 2 depicts how the frame 105 in FIG. 1 is constructed. A selected number of straight-sided porogens 108 is homogenously mixed into a batch of a liquid polymer, together forming the viscous polymer mix. Polymethylmethacrylate and polysiloxane were used as the polymer in successful reductions to practice. For purposes of this description and the claims, polymethylmethacrylate is included within the more general term "acrylic." In these illustrative embodiments the straight-sided porogens are cubic-shaped. Cubic-shaped porogens made of grains of sodium chloride were used in the reductions to practice. Particularly, grains of table salt can be used, which are typically about 250 microns to 450 microns across each cube face. After mixing the table salt into the liquid polymer, the viscous mixture was placed in a mold to cure the polymer into a solid by the application of heat and pressure. For example, without limitation, successful reductions to practice have been performed by curing the mixture for about thirty minutes at about five bars pressure in a Liquisteam-e device made by Erkodent of New Zealand. After curing the polymer into a solid, the table salt grains can then be leached out of the frame 105 by immersing the molded implant 100 in a dissolving fluid such as water or alcohol, and/or subjecting the implant 100 to a steam bath. The molded implant 100 can then be used as molded, or if necessary it can be cut and fit to a desired modified shape.

Importantly, the porogens 108 are mixed homogenously in the liquid polymer so that after curing and removing the porogens 108 the porosity is the same throughout the implant 100, from the innermost core to the outer surface. What might microscopically appear to be disconnected voids is actually the internally connected interstitial matrix, at the surface and at all levels within the implant 100. Groups of spaces 107 form the longitudinal omnidirectional capillaries from the surface to the innermost core. That is, the omnidirectional matrix ultimately interfaces a plurality of the capillaries with the attached tissue via the openings in the arcuate surface of the implant 100.

Figure 3A:
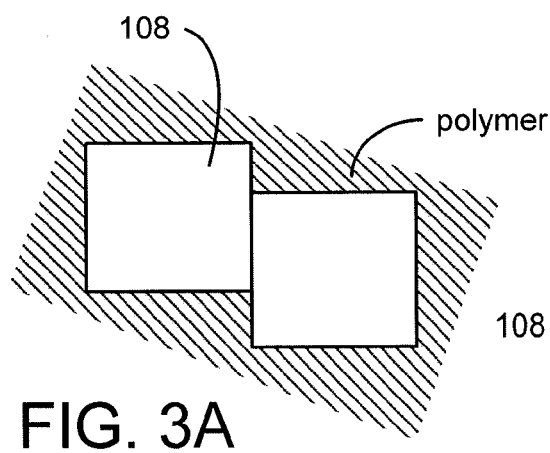
FIG. 3A diagrammatically depicts two adjacent porogens in FIG. 2.
Figure 3B:
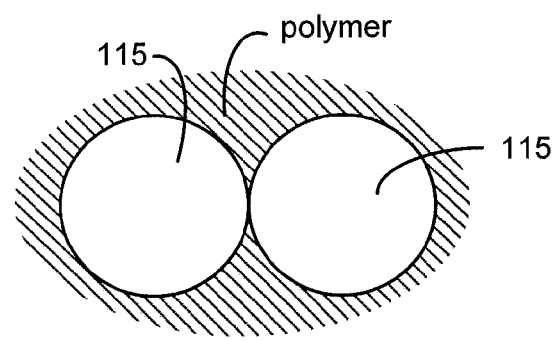
FIG. 3B comparatively shows two adjacent arcuate porogens.

FIG. 3A diagrammatically depicts why the porogens 108 are preferably straight-sided, thereby forming the planar surfaces 109 (FIG. 1) in the struts 106. Adjacent porogens 108 in the liquid polymer are urged together by the mixing action that produces the homogenous mixture. The straight-sides of adjacent porogens 108 tend to come together face-to-face as the cubes stack against each other, squeezing out the liquid polymer between them. When urged together in pressing contact, the overlapping contacting portions of the adjacent porogens 108 join the two spaces together that are created when the porogens 108 are leached out of the frame 105. This interconnecting of the spaces 107 of adjoining porogens is what creates the longitudinal extending capillaries in accordance with the present technology. In comparison, FIG. 3B depicts how two adjacent arcuate porogens 115 when urged together by the homogenous mixing would overlap only in tangential contact. The spaces created by leaching out the porogens 115 would thus only be incidentally connected, not combined into a longitudinally extending capillary as in the present technology. The depicted overlapping of the preferred straight-sided porogens 108 is merely illustrative, not limiting of the shapes of the struts 106 in the present technology. Particularly, not all the cubic porogens 108 will abuttingly engage in the face-to-face depiction of FIG. 3A. Importantly, however, it has been determined that with the use of straight-sided porogens a sufficient percentage of the porogens will create interconnected spacings that collectively produce the longitudinally extending capillaries of the present technology.

In successful reductions to practice the implant 100 was constructed by combining one part monomer to three parts polymer forming a liquid polymethylmethacrylate. The polymer was allowed to set so that polymerization would provide a desired material strength for the intended use as an anopthalmic implant. Then three parts of the salt grain porogens were mixed into one part of the liquid polymer to produce a 75% porosity. After curing the polymer and removing the porogens, tests were conducted that concluded the porous polymer was capable of superior sorptivity performance. For purposes of this description and meaning of the claims, "sorptivity" means a measure of the implant 100's capacity to absorb liquid by capillarity:

$$\text{sorptivity} = \frac{V}{A\sqrt{t}}$$

where V is the volume of absorbed liquid after a time t, and A is the cross sectional area of the wetted end of the implant. The ratio V/A is referred to as the cumulative liquid intake, an indicator of sorptivity without respect to time and with a dimension of length.

Figure 4A:
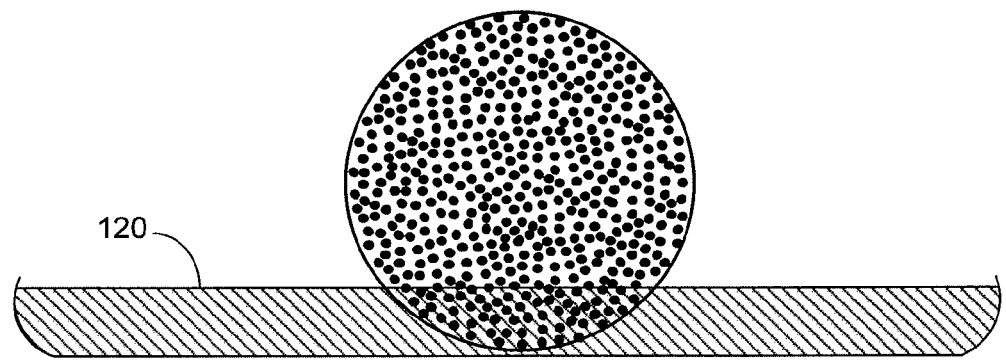
FIGS. 4A and 4B depict the implant of FIG. 1 being tested for sorptivity performance.
Figure 4B:
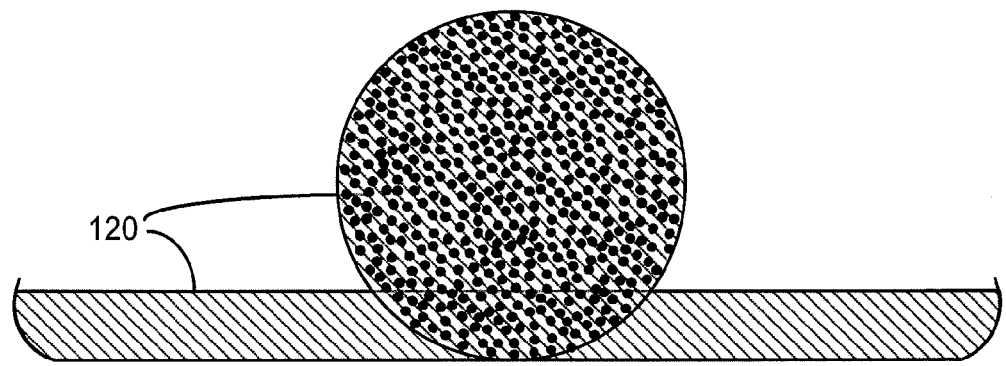

FIGS. 4A and 4B diagrammatically depict the results of experimentation that proved the superior vascularity performance of the present technology. An implant 100 constructed in accordance with this technology was placed in a shallow bath of colored water 120. About the bottom ten percent of the implant 100 was immersed in the colored water 120. FIG. 4B depicts the fact that within the time span of just hours the cumulative liquid intake in virtually all cases was the diameter of the implant 100. Particularly, in all but a few cases the implant 100 demonstrated a sorptivity capability of entirely filling the matrix with the colored water within one to four hours. In the incidental instances where the matrix was not filled during that time, the lowest observed cumulative liquid intake was about ninety percent of the implant 100's diameter. That sorptivity performance is due to the capillarity construction of the present technology that absorbed the colored water fully into the matrix even against the force of gravity.

Previously attempted solutions employing a porous polymer are unable to vascularize like the present technology, because they all lack the superior sorptivity capability of the present technology. That is the reason the previously attempted solutions fail particularly in difficult implant surgeries such as where thin or damaged tissue is involved. Where previous attempted solutions merely provide a polymer with a pore matrix, the present technology improves the fibrovascular ingrowth by absorbing the cell sustaining body fluids into matrix. The improved sorptivity of the present technology enhances the fibrovascular or bony integration with the surrounding tissue, without sacrificing structural integrity.

In some embodiments elongated carbon fibers can be added to the mixture for increased structural integrity. The carbon fiber strands in the mixture wrap around the porogens 108, strengthening the struts 106 defining the capillaries that are created by leaching the table salt from the mixture.

Figure 5:
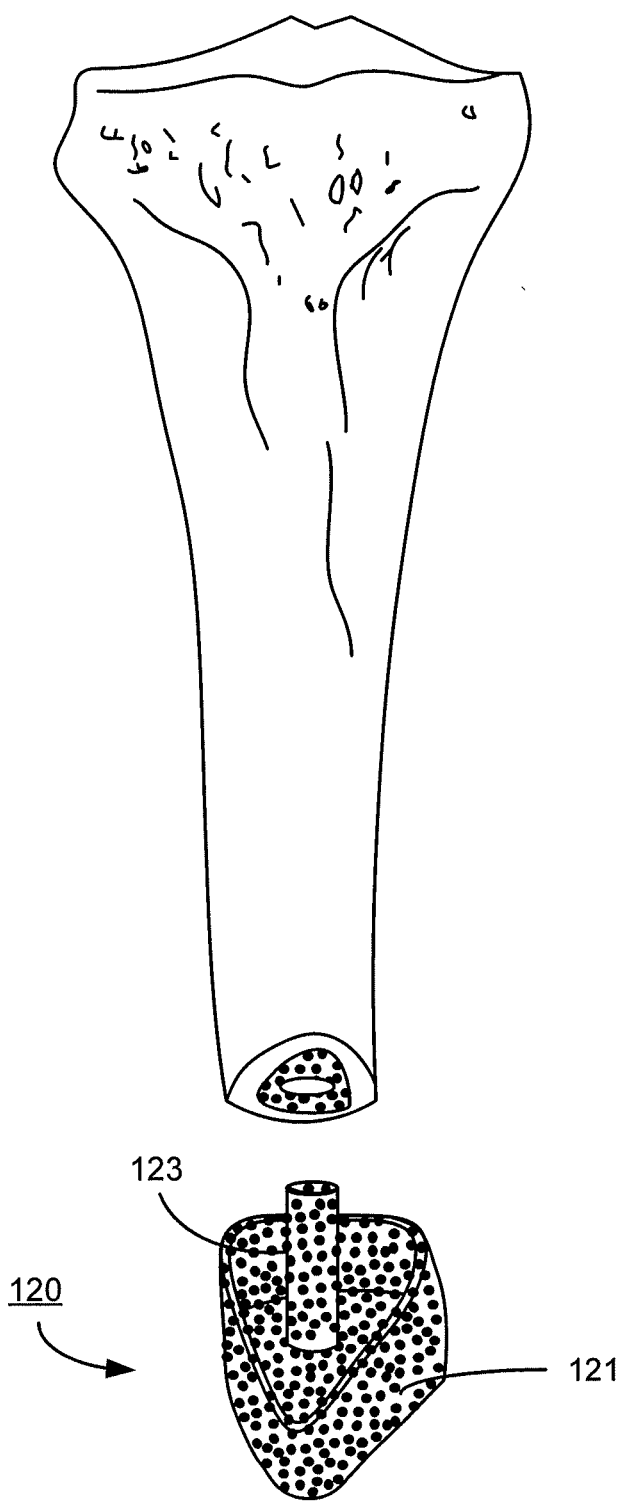
FIG. 5 depicts a bone cap implant in accordance with embodiments of the present invention.

An implant molded as described above of polymethylmethacrylate (z) is structurally rigid, nonbrittle, and has excellent water adhesion for capillarity. As such, PMMA is useful for making bone implants in accordance with this technology. For example, FIG. 5 depicts a porous PMMA cap implant 120 that is molded to have an arcuate surface 121 generally conforming to the surface of a bone. The cap implant 120 can further include a rod 123 that is sized to be receivingly disposed within the bone's medullary cavity to position and stabilize the cap implant 120. The cap implant 120 is attached to the distal end of an amputated bone to cover the exposed nerve endings, thereby providing for a more comfortable recovery from the amputation procedure. As the bone tissue integrates with the cap implant 120, a more robust bulkhead is formed for a stable attachment of a prosthetic device.

The porous polymer of this technology is also suitable for constructing fastening devices for attaching the cap implant 120 to the amputated bone. Using such fasteners promotes body tissues to more fully vascularize not only to the implant, but also to the fastener. PMMA has adequate structural integrity for use in constructing a fastener, and it can be molded into a variety of fasteners, such as but not limited to a threaded fastener shape.

Thus, in some embodiments an alloplast is contemplated with a macroporous vascularization frame 105 extending throughout, from the innermost core to the exterior surface. The porogens 108 are straight-sided, and are preferably about 250 to 400 microns across the face. Generally, it has been observed that vascularization is enabled in accordance with this technology using porogens ranging from 100 to 500 microns across the face. The vascularization frame 105 supports ingrowth of newly vascularized tissue that biologically integrates the implant with the surrounding tissue, rather than the body walling it off with a fibrous capsule. That enables the body's immune defenses to encompass the implant, to the greater extent it becomes vascularized in accordance with this technology. An integrated implant such as this is less likely to migrate, and is less likely to cause resorption of the underlying bone to which it is attached.

Use of PMMA in the present technology is advantageous because it is an inexpensive and readily available synthetic material that replicates some of the advantages of naturally occurring hydroxyapatite, which is used according to some previously attempted solutions. PMMA is an easy material for the surgeon to sterilize and use, and after implantation it provides a non-biodegradable, inert, and stable implant. PMMA can be mixed in a low viscosity if necessary in order to mold it into intricate shapes to precisely fit a particular need. When PMMA is molded into flexible shapes, the surgeon has freedom to selectively determine how to best attach the implant to the surrounding tissue. PMMA is sufficiently rigid that the implant can be altered after molding, such as by cutting or drilling, without collapsing the vascularization frame 105 structure.

The implant device material of the contemplated technology is also suitable for making entire bone implants. These porous synthetic bones because of their comparatively superior sorptivity promote body tissues to more quickly and more fully vascularize to the bone prosthesis to effectively make the bone prosthesis become a part of the body structure. These bone prostheses can fill gaps in a bone, can replace full bone voids, can replace a missing minor extremity like a finger or a toe, and can be used in plastic surgery procedures. These bone prostheses can reduce the need for a bone graft or cartilage transplant, replacing virtually any bone structure or cartilage inserted into muscle tissue. For example, these bone prostheses can be used to replace a meta tarsal or a meta carpel.

Figure 6:
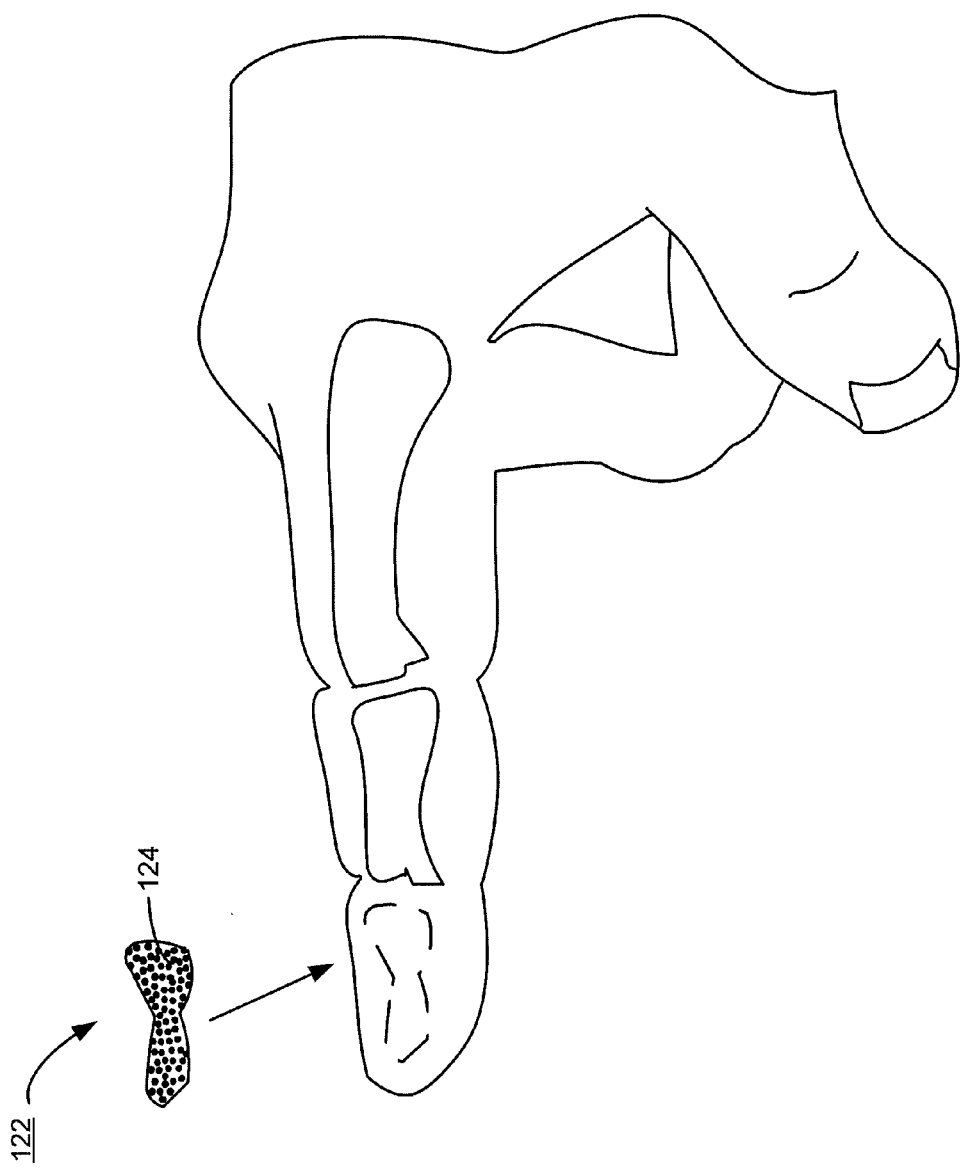
FIG. 6 depicts a digit implant in accordance with embodiments of the present invention.

For example, FIG. 6 depicts a porous digit implant 122 that is molded to have an arcuate surface 124 resembling the distal phalanx digit of a human finger. The digit implant 122 molded of the PMMA porous material can be used in a surgical procedure to replace a lost or missing digit. Normal manipulation of the finger is possible after attachment and ingrowth of the opposing flexor and extensor tendons to the digit implant 122.

Figure 7:
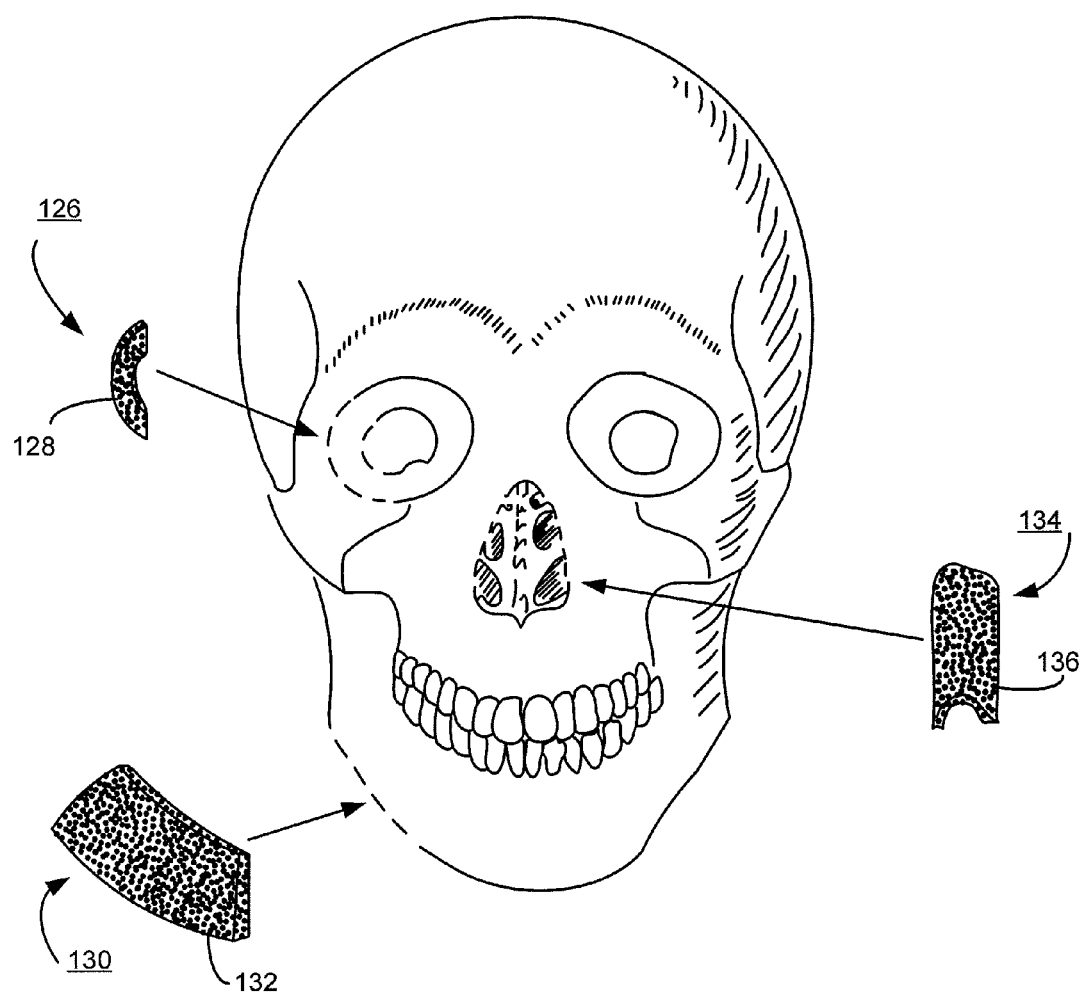
FIG. 7 depicts various maxiollfacial implants in accordance with embodiments of the present invention.

FIG. 7 depicts other implants of the present technology that are molded to have surfaces resembling bone structures that are worked on in maxillofacial surgical procedures. Generally, the porous implant of this technology can be molded into specific anatomical shapes or general shapes for chin, nasal, malar, and mandible repair or augmentation. Likewise, specific or general shapes can be molded for cranial contouring or reconstruction. For example, an implant 126 is molded to have an arcuate surface 128 resembling a portion of the orbital floor. An implant 130 is molded to have an arcuate surface 132 resembling a portion of the mandible. Yet another implant 134 is molded to have an arcuate surface 136 resembling a nasal bone for a rhinoplasty procedure.

Figure 8:
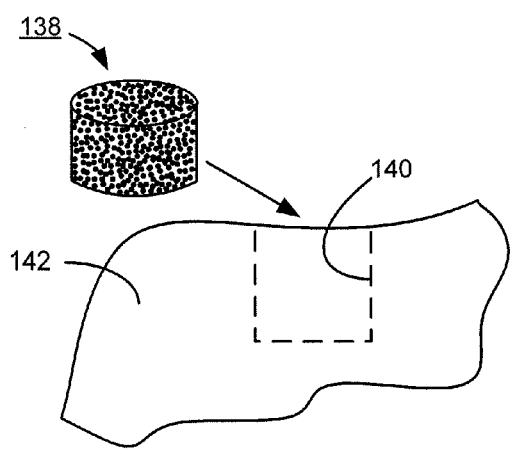
FIG. 8 depicts a cylindrical bone void implant in accordance with embodiments of the present invention.

FIG. 8 depicts yet another implant 138 of the present technology that is molded in a cylindrical shape sized to fill a void 140 in a bone 142. Various other shapes like wedges and arcs and the like can be used as gap bone replacements to fill cranium or bone voids, such as resulting from disease or trauma.

Figure 9:
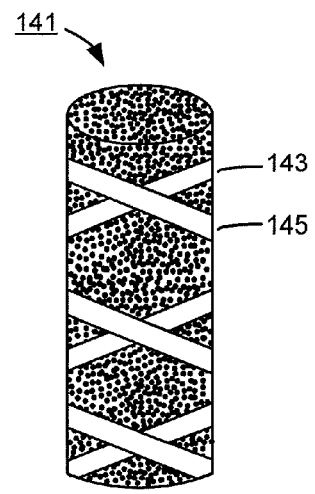
FIG. 9 depicts a bone repair implant in accordance with embodiments of the present invention.

FIG. 9 depicts an implant 141 that is likewise molded in accordance with this porous polymer technology into an elongated cylindrical shape. To strengthen the implant overlapping strips 143, 145 of a strengthening material can be attached to the exterior arcuate surface of the implant 141. For example, without limitation, the strips 143, 145 can be carbon fiber material. In these illustrative embodiments the strips 143, 145 cover only a portion of the entire arcuate surface, exposing windows of the porous polymer material to increase the surface area to which tissue can vascularize to the implant 141.

Figure 10:
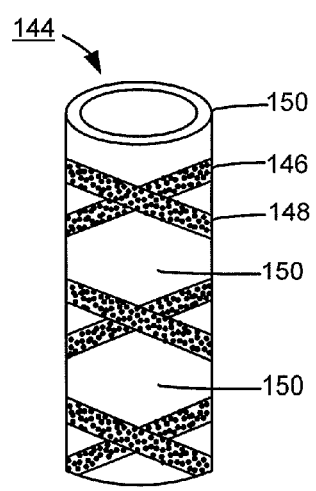
FIG. 10 depicts another bone repair implant in accordance with embodiments of the present invention.
Figure 11:
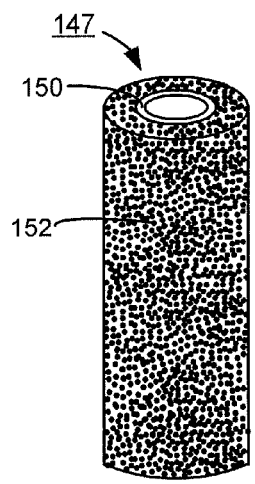
FIG. 11 depicts another bone repair implant in accordance with embodiments of the present invention.

FIG. 10 depicts an implant 144 having overlapping strips 146, 148 of the porous polymer material of the present technology attached to a rod 150. The rod 150 is for purposes of strengthening a broken bone, and as such can be constructed of an adequately strong material such as carbon fiber, stainless steel, titanium, and the like. In these illustrative embodiments the porous polymer strips 146, 148 cover only portions of the rod 150, leaving windows of exposed surfaces of the rod 150. Alternatively, FIG. 11 depicts another implant 147 having a layer of the porous polymer material of the present technology covering the entire longitudinal surface of the rod 150. Although not depicted, it will be understood that the implant 141 in FIG. 9 can likewise be constructed to have the rod 150 for additional strength.

Figure 12:
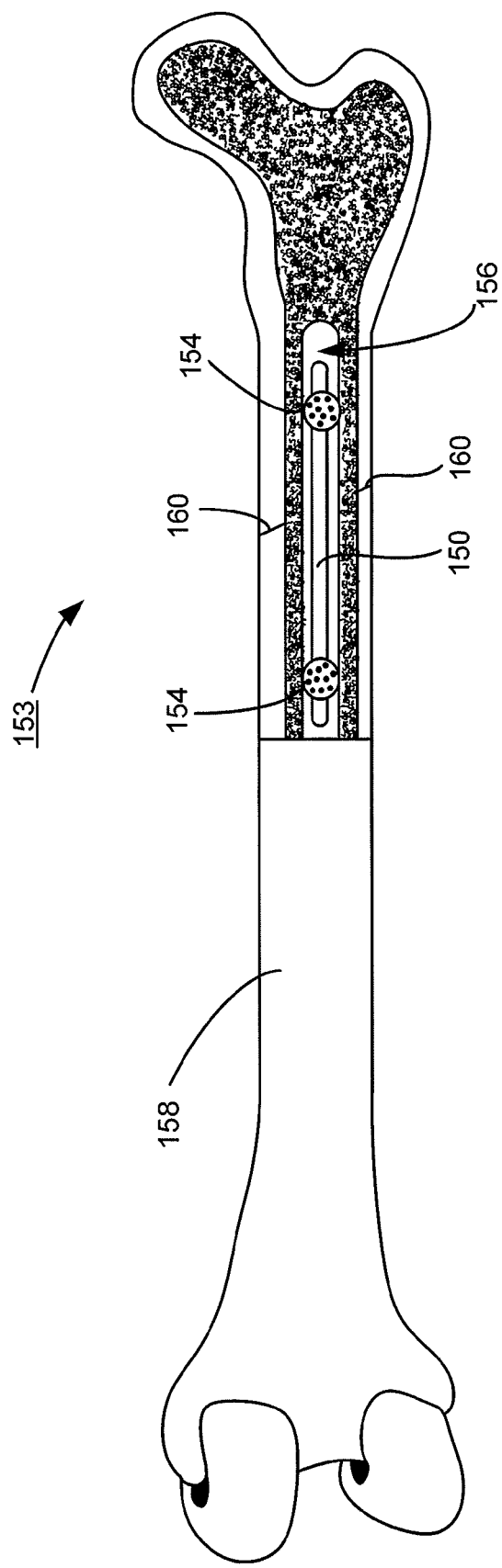
FIG. 12 depicts another bone repair implant in accordance with embodiments of the present invention, depicted within the medullary cavity in a bone.

FIG. 12 depicts embodiments of yet another implant 153 that has two spheres 154 of the porous polymer of the present technology attached to the rod 150. The rod 150 and spheres 154 are depicted as having been placed into the medullary cavity 156 of a bone 158. The implant 153 spans a fracture 160 in the bone 158. The rod 150 is preferably hollow to provide a path for the flow of bone marrow along the medullary cavity 156.

Figure 13:
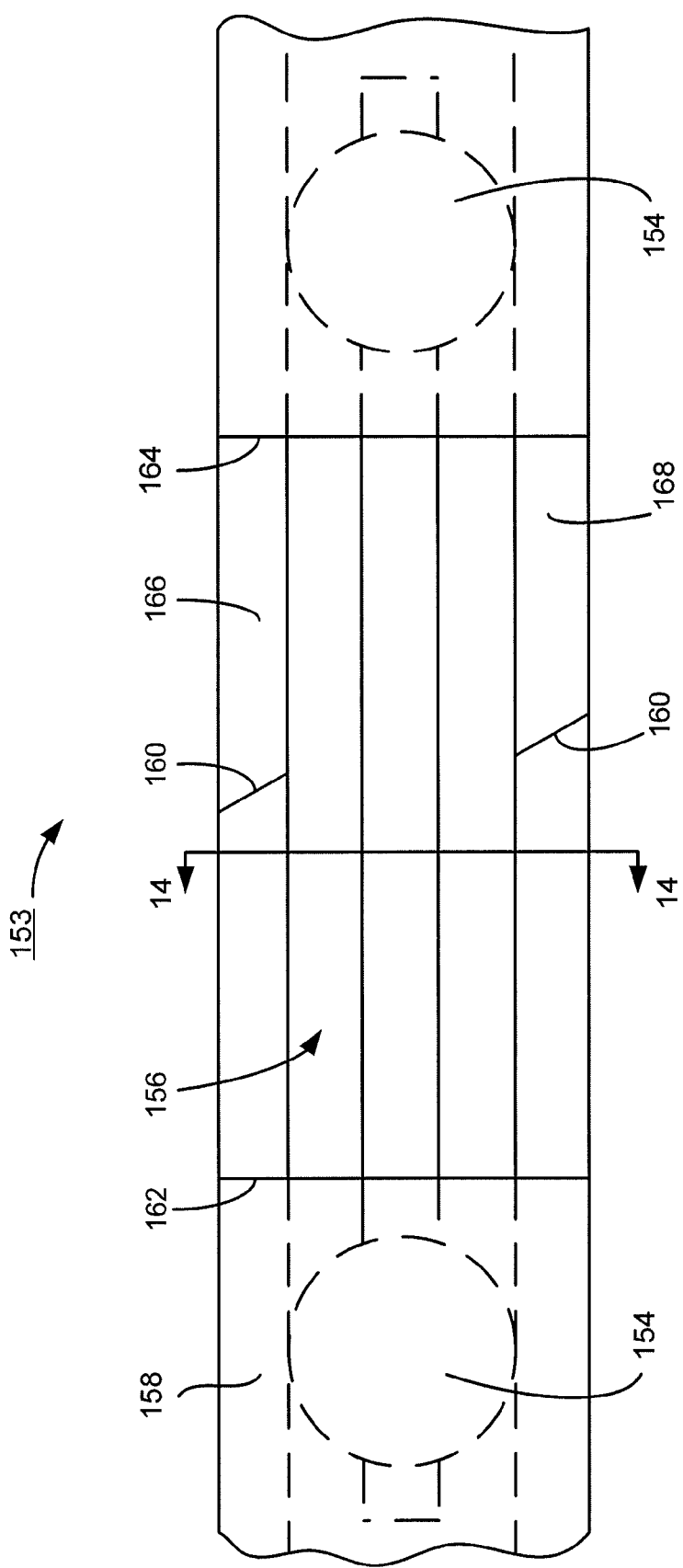
FIG. 13 is an enlarged detail of a portion of FIG. 12.

FIG. 13 is an enlarged portion of the fractured bone 158 in FIG. 12, more particularly depicting how it can be repaired in accordance with the embodiments of the present invention. Cuts 162, 164 are made through the periosteum and the compact bone wall, and then the cuts 162, 164 are connected by cuts 166, 168 to create a removable section of the bone (not depicted) to expose the medullary cavity 156. The spheres 154 can have internal openings that are sized to frictionally engage the outer surface of the rod 150 to affix the sphere 154 to the rod 150. A particular sphere 154 can be selected from a set of different size diameter spheres, to match the diameter of the medullary cavity 156. The size of the sphere 154 is selected to anchor the implant 153 within the medullary cavity 156.

Figure 14:
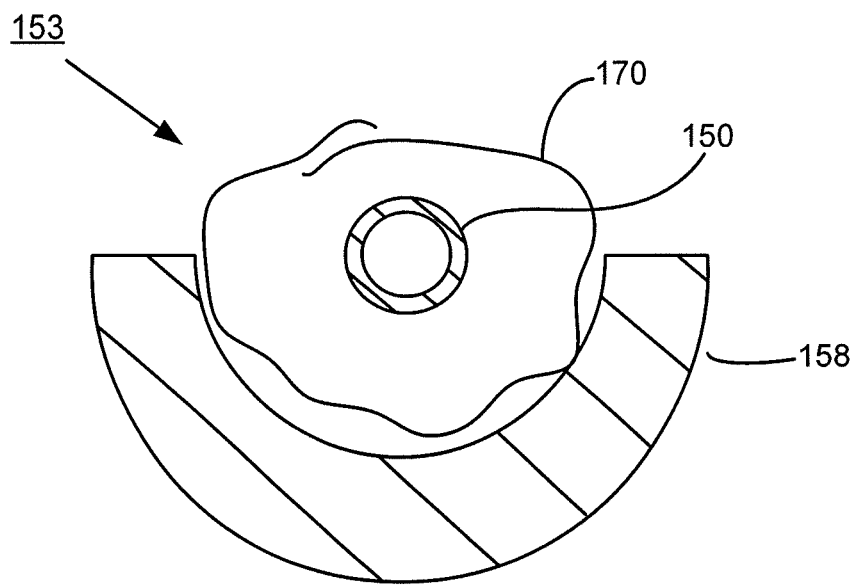
FIG. 14 is a cross sectional depiction taken along the section line 14-14 in FIG. 13.

Two or more such selected size spheres 154 are affixed to the rod 150. One end of the rod 150 is slid into the medullary cavity 156 until the other end clears the respective cut 162, 164. That end of the rod 150 is then slid within the medullary cavity 156 to substantially center the fracture 160 among the spheres 154, or otherwise as desired. FIG. 14 is a cross sectional view of the implant 153 taken at the section line 14-14 in FIG. 13, depicting how a carbon fiber wrap 170 can envelope the exposed portion of the implant 153 to strengthen the bone 158 at the fracture 160 during healing. After the implant 153 is inserted in place, the removed section of bone can be reattached with adhesive. This permits the repair of a significant bone injury with no need for the use of any screws, pins, plates, and the like that are customarily used in previously attempted solutions.

Figure 15:
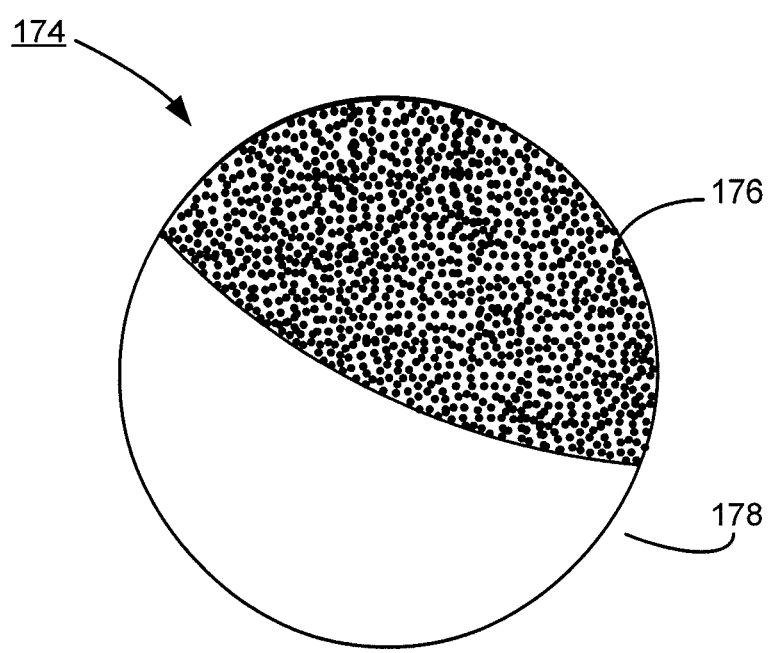
FIG. 15 is similar to FIG. 1 but depicting another spherical implant in accordance with embodiments of the present invention.

Returning momentarily to the illustrative embodiments of FIG. 1, it will be understood that PMMA is a particularly hard material, making it difficult to suture directly to it. To aid in suturing, suture tunnels 172 can be drilled into the implant 100 as a secondary manufacturing operation after the molding procedure. Alternatively, FIG. 15 depicts an ophthalmic implant 174 that is constructed in accordance with alternative embodiments in which a porous PMMA partial sphere 176, molded as described above, is attached to another partial sphere 178 made of a different material that better facilitates suturing directly thereto. The partial spheres 176, 178 are complimentary in that when they are joined together they form a spherical shape resembling a human eye. The partial sphere 178 in successful reductions to practice has been molded of a polysiloxane. The partial spheres 176, 178 can preferably be connected together by thermal fusion with no need for an adhesive or other type of fastener.

Figure 16:
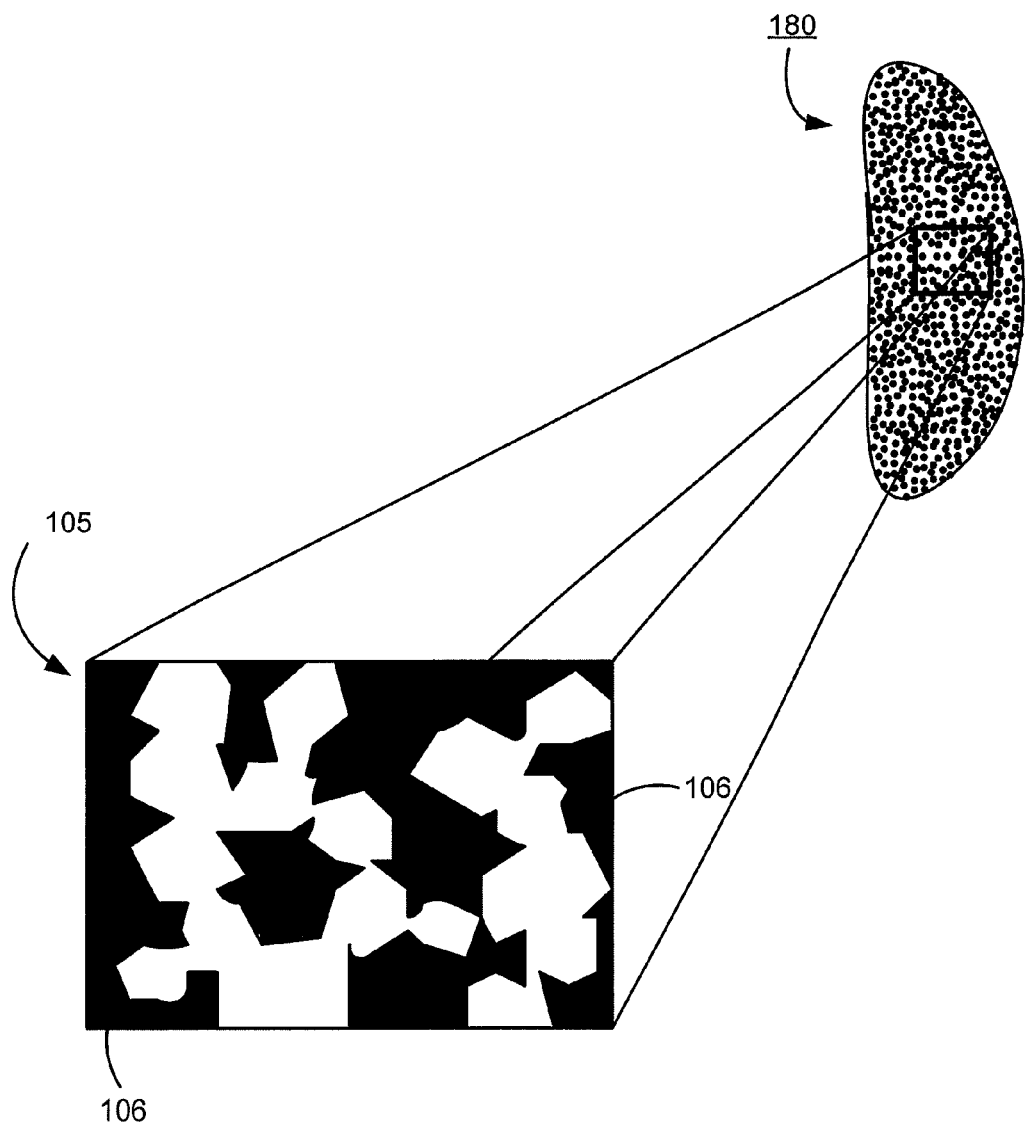
FIG. 16 is a side depiction of a mammary augmentation implant in accordance with embodiments of the present invention.

FIG. 16 is a side view of an implant 180 constructed in the same manner as described above but with a softer polymer, such as a polysiloxane blend, to produce a porous polymer that is suited for augmenting human muscle tissue. Note from the enlarged detail portion the vascularization frame 105 is constructed of the struts 106 formed by using straight-sided porogens during the molding process, as described above. That gives the implant 180 the superior sorptivity capability in accordance with the present technology. The frame 105 and matrix constructions extend throughout the implant 180, as described above. The implant 180 can be used to augment tissue in a mammary augmentation procedure.

These are but a few examples of the types of alloplastic implants that can be constructed in accordance with this technology. Other uses will be clear to the skilled artisan having read this disclosure. For example, without limitation, implants according to this technology are useful for augmenting areas of the chest, the hip, the ear, and the penis. A complete enumeration of all such types of implants is unnecessary for the skilled artisan to understand the scope of the claimed invention, and so no such enumeration is implied. In all events, to augment or repair body tissue a surgical procedure is performed to incise the affected tissue and dissect or otherwise remove any defective or diseased tissue. An appropriately shaped implant, either molded to shape or formed from a molded generic shape of porous polymer, is placed into the incised tissue to provide the augmentation or repair. Typically, the implant is surgically attached to the surrounding tissues via fasteners, wires, sutures, and the like which can also be advantageously constructed of the porous polymer of the disclosed technology. The overlying tissues are repositioned over the implant and the body is closed according to standard surgical techniques. The selected shape of the implant provides the desired volume augmentation and structural integrity to the affected tissue, and the vascularization that integrates the implant with the surrounding tissue provides the desired motility and nonmigration in support of the desired functionality of the implant.

In some embodiments additives can be used in the frame 105 to enhance the tissue ingrowth and osteo integration, such as stem cells and cell growth products. In some embodiments titanium powder can be added to the mixture, which has been observed to stimulate increased vascularization of body tissue to the implant device.

While the preferred embodiments have been described herein, those skilled in the art will recognize that certain details may be changed without departure from the spirit and scope of the invention. Thus, the foregoing specific embodiments and applications are illustrative only and are not intended to limit the scope of the invention. It is to be understood that even though numerous characteristics and advantages of various embodiments of the described technology have been set forth in the foregoing description, together with the details of the structure and function of various embodiments of the invention, this disclosure is illustrative only, and changes may be made in detail, especially in matters of structure and arrangement of parts within the principles of the described technology to the full extent indicated by the broad general meaning of the terms in which the appended claims are expressed. For example, other polymers and porogens are contemplated while still maintaining substantially the same functionality without departing from the scope and spirit of the claimed invention. Further, although the illustrative embodiments described herein are directed to surgical implants, and related technology, it will be appreciated by those skilled in the art that the claimed invention can be applied to other devices employing a porous material as well without departing from the spirit and scope of the described technology.

What is claimed:

1. A porous orbital implant comprising a size and a substantially spherical shape resembling a human eye, the orbital implant comprising a nonbiodegradable acrylic polymer that is molded to form an omnidirectional vascularization frame defining a porous arcuate external surface and a plurality of internal longitudinally-extending and interconnected interstitial capillaries extending from an innermost core of the implant to said porous arcuate external surface, the interconnected interstitial capillaries of a substantially constant porosity throughout the implant, the internal capillaries in fluid communication with the external porous surface and thereby configured to absorb a fluid adjacent the implant, wherein the interconnected interstitial capillaries are configured to increase the sorptivity capability of the orbital implant, wherein the acrylic polymer is formed from a liquid polymer that is homogenously mixed with grains of a cubic-shaped porogen and then cured into a solid polymer and porogen mixture, the interconnected interstitial capillaries defined entirely by leaching out the grains of the porogen from the solid polymer after curing, wherein the acrylic polymer is selected from the group consisting of polysiloxane and polymethylmethacrylate, and wherein the porogen is table salt.

2. The orbital implant of claim 1 comprising an additive configured to accelerate vascularization of tissue with the frame.

3. The orbital implant of claim 1 wherein the acrylic polymer prior to being molded is liquid polymethylmethacrylate.

4. The orbital implant of claim 3 wherein the acrylic polymer prior to being molded is mixed one part of the liquid polymethylmethacrylate to about three parts of the porogen.

* * * * *